(12) United States Patent
Foster

(10) Patent No.: US 8,403,824 B2
(45) Date of Patent: Mar. 26, 2013

(54) HEART ASSIST APPARATUS

(75) Inventor: Graham Foster, Swansea (GB)

(73) Assignee: Calon Cardio Technology Limited, Swansea (GB)

( * ) Notice: Subject to any disclaimer, the term of this patent is extended or adjusted under 35 U.S.C. 154(b) by 120 days.

(21) Appl. No.: 13/058,040

(22) PCT Filed: Aug. 10, 2009

(86) PCT No.: PCT/GB2009/001954
§ 371 (c)(1),
(2), (4) Date: Feb. 8, 2011

(87) PCT Pub. No.: WO2010/015836
PCT Pub. Date: Feb. 11, 2010

(65) Prior Publication Data
US 2011/0144413 A1    Jun. 16, 2011

(30) Foreign Application Priority Data

Aug. 8, 2008   (GB) .................................. 0814536.9
Dec. 5, 2008   (GB) .................................. 0822235.8
Mar. 11, 2009  (GB) .................................. 0904188.0

(51) Int. Cl.
*A61N 1/362* (2006.01)

(52) U.S. Cl. ........................................................ 600/16
(58) Field of Classification Search ............... 600/16–18
See application file for complete search history.

(56) References Cited

U.S. PATENT DOCUMENTS 6,688,861 B2 *   2/2004   Wampler .................... 417/423.7
2004/0234397 A1   11/2004  Wampler

FOREIGN PATENT DOCUMENTS

| EP | 0599138 A2 | 6/1994 |
| EP | 1323438 A2 | 7/2003 |
| WO | 98/04834 A1 | 2/1998 |
| WO | 2007/140481 A2 | 12/2007 |

* cited by examiner

*Primary Examiner* — Scott Getzow
(74) *Attorney, Agent, or Firm* — Larson & Anderson, LLC

(57) ABSTRACT

The apparatus is a ventricular assist device comprising: a pump with a housing having therein radial a impeller, and a rotor for driving the impeller, both the rotor and the impeller being hydrodynamically suspended within the housing in us, the pump further including a stator for driving the rotor; an inlet cannula section arranged to extend from an internal part of the ventricle to straddle the wall of the ventricle, the stator being within the inlet cannula section to be located in the internal part of the ventricle; and an outlet for blood driven by the impeller such that the pump is a radial pump. Both the outlet and the impeller are arranged to reside outside of the heart.

24 Claims, 18 Drawing Sheets

HEART ASSIST APPARATUS

This application is the US national stage of PCT/GB2009/001954 filed Aug. 10, 2009, which claims priority to GB0814536.9 filed on Aug. 8, 2008, GB08022235.8 filed on Dec. 5, 2008, and GB0904188.0 filed on Mar. 11, 2009, which are incorporated by reference.

The present invention concerns implantable heart assist apparatus, such as a ventricular assist device.

Heart Failure is major global health problem resulting in many thousands of deaths annually. Until recently the only way to treat advanced heart failure has been by heart transplant or implantation of a mechanical heart. Unfortunately, donor hearts can only meet a tiny fraction of the demand and totally mechanical hearts have yet to gain widespread acceptance due to their associated technical difficulties.

Ventricular assist devices (VADs) have gained increased acceptance over the last three decades primarily as a bridge to transplant devices. VADs are implanted long term and work alongside a diseased heart to boost its output and keep the patient alive and/or give a better quality of life whilst awaiting transplant. The use of VADs has had an unexpected result in some patients: the reduction in strain on the heart over time has led to significant spontaneous recovery of the ventricle. This gives hope to many patients for whom a donor heart may not become available because early implantation of a VAD may allow patient recovery before the disease reaches the most advanced stages. It is also a far more preferable outcome to have one's own heart recover than undergo a transplant—even if donor hearts are available.

The main reasons preventing VADs from being fitted on a more routine basis are the highly invasive surgical procedure required to fit the devices, and the high cost of the devices themselves.

Typically, a sternotomy, full heart lung bypass, and major procedures to the heart and thoracic aorta are required to fit a VAD. Presently the risk of such an operation cannot only be justified for those in the most advanced stages of Heart Failure. With regard to cost, current devices are typically of complex construction and require specialised and expensive manufacturing processes for their construction. The surgery required to fit them is also expensive because it is long and intensive.

If the long term implantation of a VAD or an equivalent circulatory assist device could be achieved with a less invasive surgical procedure, and the cost of the devices could be significantly reduced, then the use of VADs to treat heart failure in its earlier stages could become far more widespread and routine.

The key to a less invasive implantation procedure for a VAD is to make the device as small as possible so that it can be implanted using a procedure that requires only a small initial incision. Furthermore, it should be possible to implant or connect the device to the heart whilst the heart is still beating and not require a bypass.

It is also important to minimise surgical risks so it is beneficial to use existing proven techniques, improving on them where possible. A well proven method of implanting current VADs is attaching the devices to the apex of the left ventricle, with an inlet to the device residing within the ventricle and the outlet of the device sitting outside of the heart. The workings of the pump (impellor, motor, etc) may reside mostly within the ventricle, across the ventricle wall, or mostly outside of the ventricle depending on the design of the device.

The procedure can be carried out via a thoracotomy rather than sternotomy if the device size is small enough—with a significant reduction in surgical trauma.

One feature of the technique of attaching a VAD to the apex of the ventricle that is undesirable is the need to core the apex of the heart to accommodate the part of the pump that sits across it. It is therefore beneficial to minimise the size of this core as the smaller the core the less trauma results. Also, the size of the core can be a limit on the patient population suitable for the device. For example, small adults and juveniles cannot be fitted with some current pumps as their hearts are not large enough to accommodate the core size.

Another important requirement of VADs is that they must be near wearless in operation so that they need not be serviced for many years. Traditional bearings are not suitable as they eventually wear and change the performance characteristics of the VAD. Hydrodynamic suspension of the rotating parts of the pump eliminates the need for traditional bearings and ensures that moving and fixed parts of the pump never make physical contact.

There is a continuing need to develop improved ventricular assist devices. According to the invention, therefore, there is provided an implantable heart assist apparatus such as a ventricular assist device, for attachment to the apex of the heart, the apparatus having hydrodynamically suspended moving parts and comprising an impeller and outlet that reside outside of the heart, and a combined motor and inlet cannula section that straddles the wall of the ventricle and extends into the ventricle itself. The motor rotor components are attached to the impeller and extend into the inlet cannula. The motor stator components are integrated into the inlet cannula adjacent to the rotor components.

The above layout provides significant advantages and allows a number of desired considerations to be achieved as follows:

positioning the impeller outside of the heart in a location where there is greater space available allows a larger diameter of impeller to be used, with consequently improved efficiency; and integrating the motor components into the inlet cannula provides a convenient position for the motor that does not increase the overall size of the pump.

In preferred embodiments (see for example, the embodiments of FIGS. 1 to 6, 8, 9, 10, 11, 13 and 14), the apparatus has a first blood path from the inlet to the outlet via the impeller, and a second blood path comprising spacing between the rotor and stator. In some embodiments, the second blood flow path may be smaller in capacity to that of the first blood path; in other embodiments, as will be described in the following description with reference to FIGS. 14 and 15, the second blood path may be comparable in capacity to that of the first blood path so that together they form a split main blood path.

Especially in the latter embodiments, it is preferred that the stator has a series of longitudinally extending grooves on a inner face thereof which defines the portion of the blood path from the inlet to the outlet. It is further preferred that respective lands between adjacent ones of the grooves are provided with hydrodynamic bearings for the stator. Such grooves are typically parallel to one another and furthermore they preferably extend parallel to a central axis of the stator.

In further preferred embodiments of the invention, the impeller comprises a plurality of impeller blades and shrouds for the respective impeller blades. Such shrouds preferably comprise a series of alternating front shrouds for alternate even-numbered ones of the blades and alternating rear shrouds for alternate odd-numbered ones of the blades. In this arrangement, adjacent blades are generally connected to one another by the respective alternating shrouds (that is, a front shroud connects adjacent front edges of the blades, and a rear shroud connects the next adjacent rear edges of the blades). In such an arrangement, the impeller has a cross-section of castellated shape, with alternating front and rear shrouds forming respective raised and lowered castellations.

This arrangement is particularly suited to the incorporation of hydrodynamic bearings on the front or outward faces of the alternating shroud (the faces of the shrouds that are adjacent to the respective faces of the pump casing). The bearings would typically be tapered so as to provide a decreasing clearance between the shroud and the casing in the direction of rotation.

In this latter arrangement, it is particularly preferred to incorporate motor rotor magnets into the alternating shrouds, as will be described below with reference to FIGS. 16 to 18 of the accompanying drawings.

In further preferred embodiments of the invention (see, for example, FIGS. 10 to 12), the impeller may be provided with means for magnetically biasing the impeller towards the stator. This can enable a one-sided hydrodynamic bearing to be provided (that is, only on the face of the impeller which is closer to the stator).

In still further preferred embodiments of the invention (see, for examples, FIGS. 8, 9, 10 to 12 and 18), the impeller may be of a unitary body of magnetisable material, having magnetised zones, which may include motor magnetised zone(s) for motor function and optionally magnetised zone(s) to bias the entire rotor axially.

In some embodiments (see, for example, FIGS. 19 to 21), the pump chamber is located outside of the heart, an inlet cannula is to be located across the wall of the heart and the motor body is to be located within the heart.

Embodiments of the invention and preferred features thereof will now be described in more detail, with reference to accompanying drawings, in which.

Figure 1:
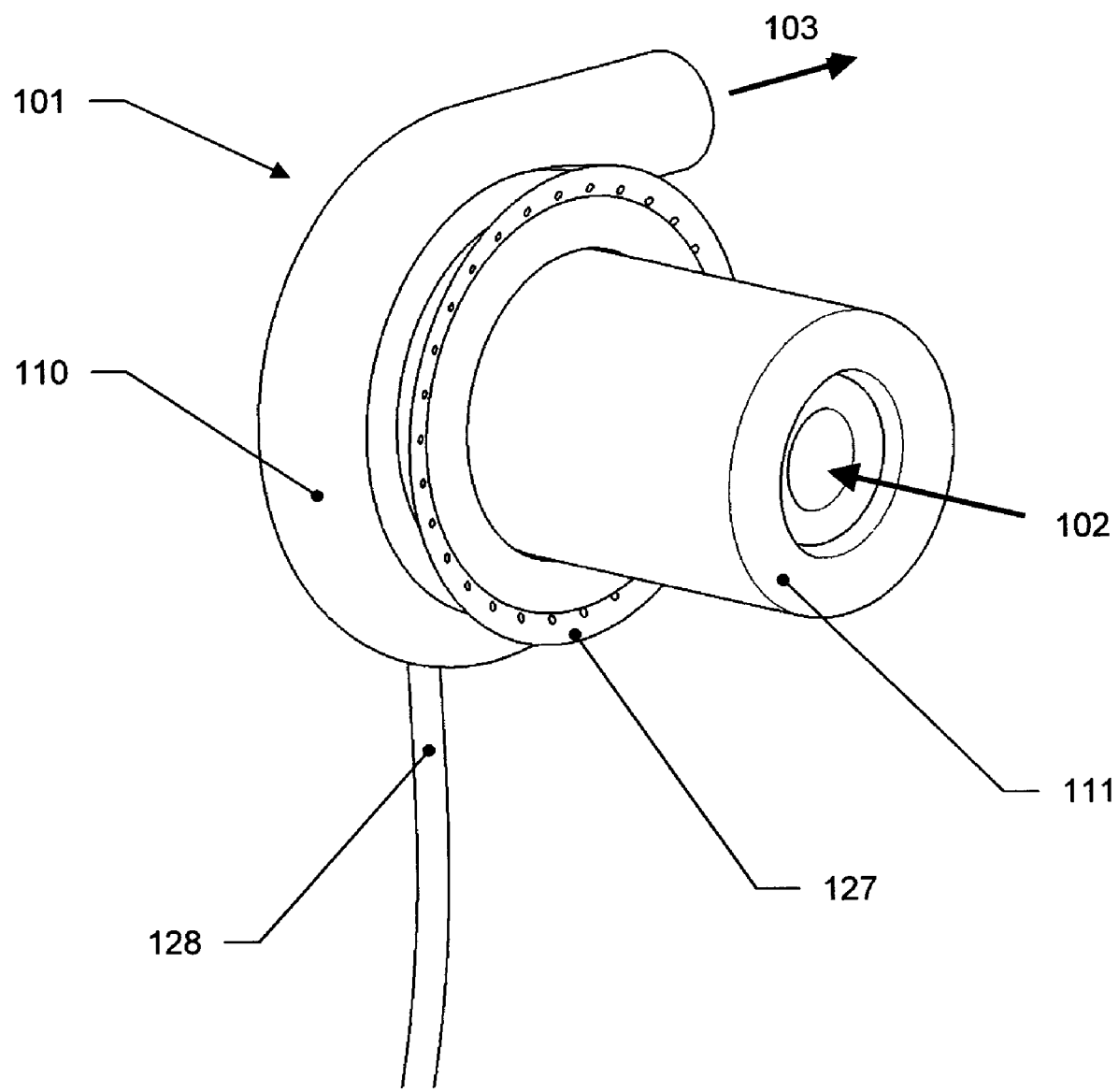
FIG. 1 is a perspective view of a first embodiment of a VAD according to the invention.

FIGS. 1 to 6, in which like parts are denoted by like reference numerals, show a first embodiment of a VAD according to the invention. The VAD has a pumping chamber 101 with an inlet 102 for blood, and an outlet 103 for blood. A primary blood flow path 104 is defined between the inlet 102 and the outlet 103.

When implanted (see FIG. 2), the pumping chamber 101 resides outside of the heart on the apex 105 of the ventricle with its outlet 103 connected to an outflow cannula 106 which is in turn grafted to the descending aorta 107. It is also possible to graft the outflow cannula 106 to the ascending aorta 108 (graft not shown). The pumping chamber 101 includes an impeller 109 which is preferably of a radial or mixed flow type and a volute 110 which aids the conversion of kinetic energy to thus improving efficiency.

The positioning of the pumping chamber 101 outside of the heart allows it to be significantly larger than would be possible if it were implanted into the heart. This arrangement enables both the impeller 109 and volute 110 to be of an optimised design to the benefit of both pumping capacity and efficiency.

An inflow cannula 111 extends from the pumping chamber 101, through the wall of the ventricle 112 into the chamber of the ventricle 113, so that the inlet 102 for blood is completely within the chamber of the ventricle 113.

The pumping chamber 101 is enclosed by a casing that comprises a front face 114 that is adjacent to the inflow cannula 111, and a rear face 115 that is opposite to the inflow cannula.

The impeller 109 has a series of impeller blades 116 (see FIG. 3 and FIGS. 5 and 6) that are connected by an alternating shroud that alternately bridges the gap between blades 116 on their front and rear edges. Therefore a series of front shrouds 117 are created on the side of the impeller adjacent to the inflow cannula 111, and a series of rear shrouds 118 are created on the side of the impeller opposite to the inflow cannula 111.

The faces on the front shrouds 117 and rear shrouds 118 are large enough to accommodate hydrodynamic bearings 124 for the axial centralisation of the impeller 109. As the hydrodynamic bearings 124 face in opposite directions, the rotor can be fully constrained axially.

The alternating shroud arrangement provides advantages over traditional shroud arrangements, particularly in the application of blood pumps. Traditional shrouds usually take the form of complete discs that can be single or double sided (i.e. front or rear shrouds, or both). These known shrouds therefore create a trapped space behind them, which can lead to areas of low flow and high shear stress, factors which increase the likelihood of undesirable haemolysis and thrombosis.

The alternating shroud layout used in the embodiment described is also more amenable to the incorporation of hydrodynamic bearings. The discrete segments created by each shroud section allow a clear start and finish to the hydrodynamic bearings and therefore the bearing design can be optimised.

Typically the hydrodynamic bearings are designed with tapered (decreasing) clearance between the shroud and the casing with respect to the direction of rotation.

The motor that powers the VAD is integrated into the inlet cannula 111. The motor rotor 119 is constructed from a tubular member extending the length of the inlet cannula from the impeller 109 to the inlet 102, and contains permanent magnets 120. The motor stator 121 is constructed from a larger diameter tubular member that extends from the rear casing 115 to the inlet 102. and contains coils 122 and laminations 123 (see FIGS. 3 and 4).

A clearance between the rotor 119 and stator 121 allows a secondary flow 125 between the two parts, thereby creating a radial hydrodynamic bearing 126 for the radial centralisation of the rotor 119. The combination of radial and axial hydrodynamic bearings restrains all degrees of freedom and means that no further centralisation means is required.

The radial hydrodynamic bearing 126 may be created by the natural hydrodynamic journal effect of the rotor 119 rotating within the stator 121 with a tight clearance; alternatively additional hydrodynamic bearing members (not shown) may be included to increase the hydrodynamic bearing forces.

The VAD is attached to the heart by a sewing ring 127 which would typically be attached to the outside of the apex 105 of the ventricle by means of sutures, a tissue compatible adhesive, a combination of the two or another suitable attachment method. A sealing felt (not shown) may be trapped between the sewing ring 127 and the apex 105 to form a blood tight seal around the emergence of the inflow cannula 111 from the apex 105.

Electrical power is supplied by way of an electrical cable 128 and connector 129. The electrical cable can either be routed percutaneously to an external console and power supply or to an implanted inductive coil for transcutaneous power transfer. Speed control electronics 130 may also be integrated taking advantage of the space available outside of the heart.

Figure 7:
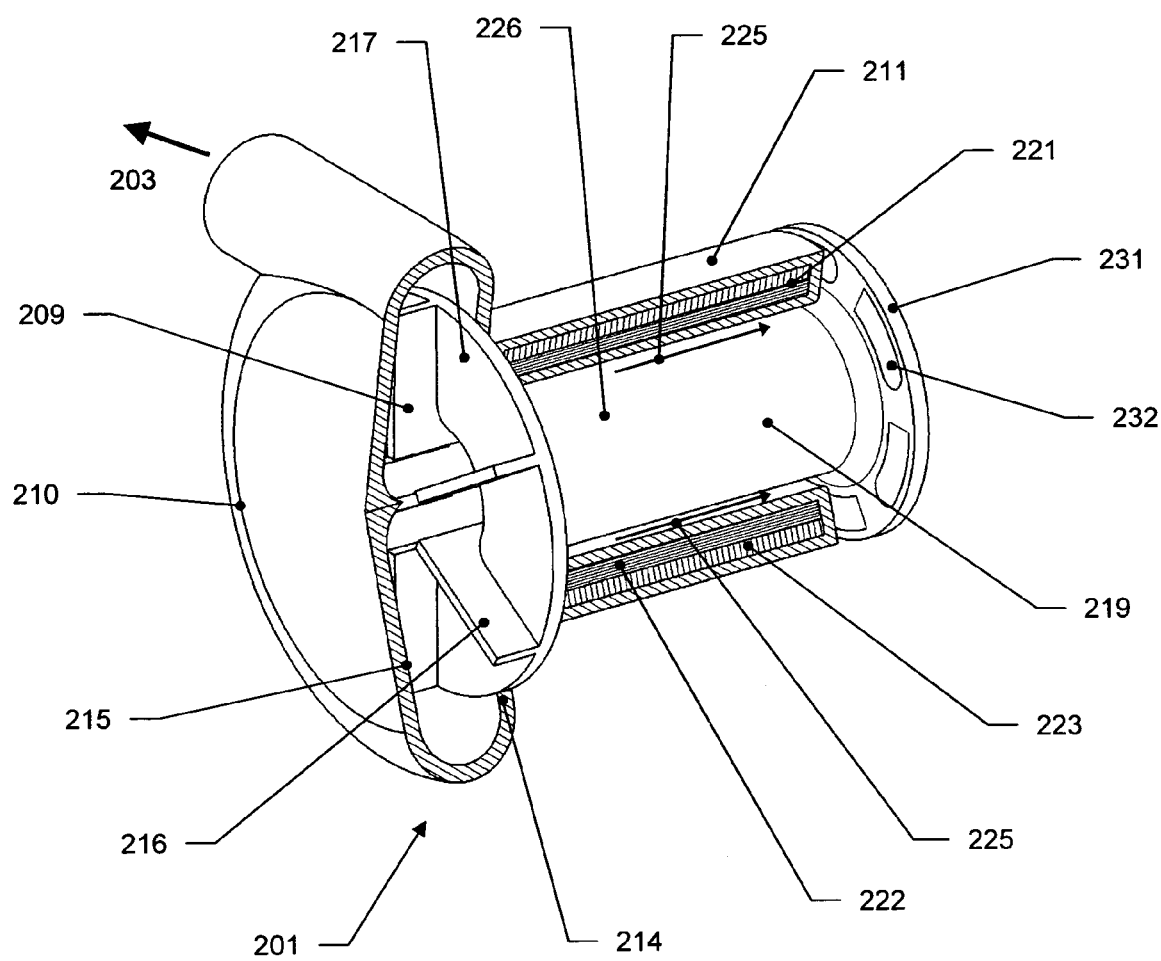
FIG. 7 is a perspective cutaway view of a second embodiment of a VAD according to the invention.
Figure 8:
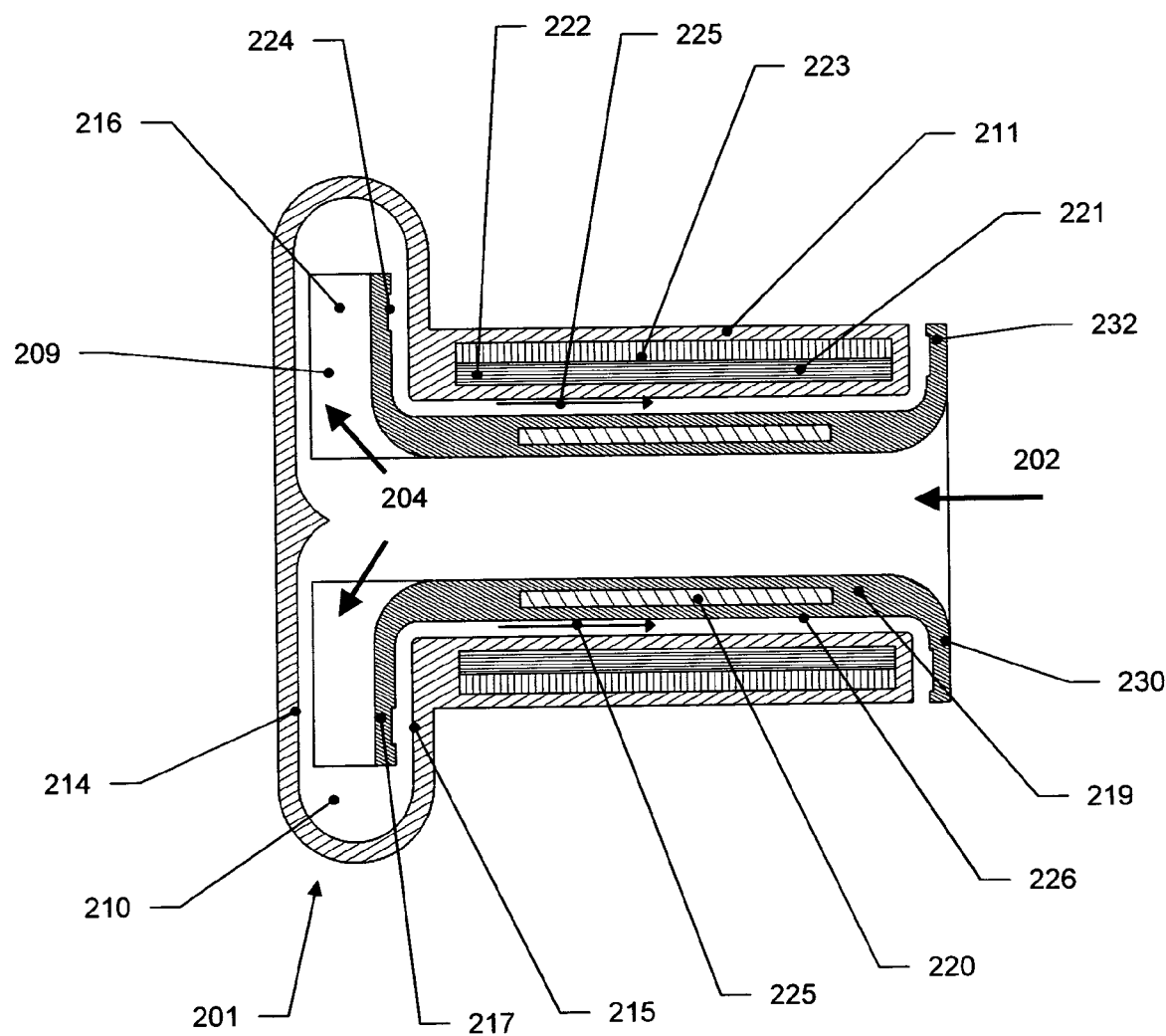
FIG. 8 is a full sectional view of the VAD of FIG. 7.

FIGS. 7 and 8 show a second embodiment of the invention, which is similar to that of FIGS. 1 to 6, but which differs in the nature of the impeller and the axial hydrodynamic bearings.

Instead of the alternating front shroud 117 and rear shroud 118 on the impeller 109 of FIGS. 1 to 6, the impeller 209 of FIGS. 7 and 8 has a single front shroud 217. Hydrodynamic bearings 224 on the front face of the front shroud 217 resist axial forces tending to push the impeller 209 towards the inlet 202. As there are no hydrodynamic bearings on the rear of the impeller 209, a flange 231 on the inlet 202 side of the rotor 219 is provided with hydrodynamic bearings 232 that are able to resist axial forces tending to push the impeller 209 away from the inlet 202.

Therefore the above hydrodynamic bearings are able to act as a pair to centralise the impeller 209 axially and resist axial forces from either direction. The radial hydrodynamic bearing 226 works as per the embodiment of FIGS. 1 to 6 so as to resist radial forces and in combination with the axial hydrodynamic bearings restrain all degrees of freedom.

All other aspects of the embodiment of FIGS. 7 and 8 operate in a similar manner to the embodiment of FIGS. 1 to 6.

Figure 9:
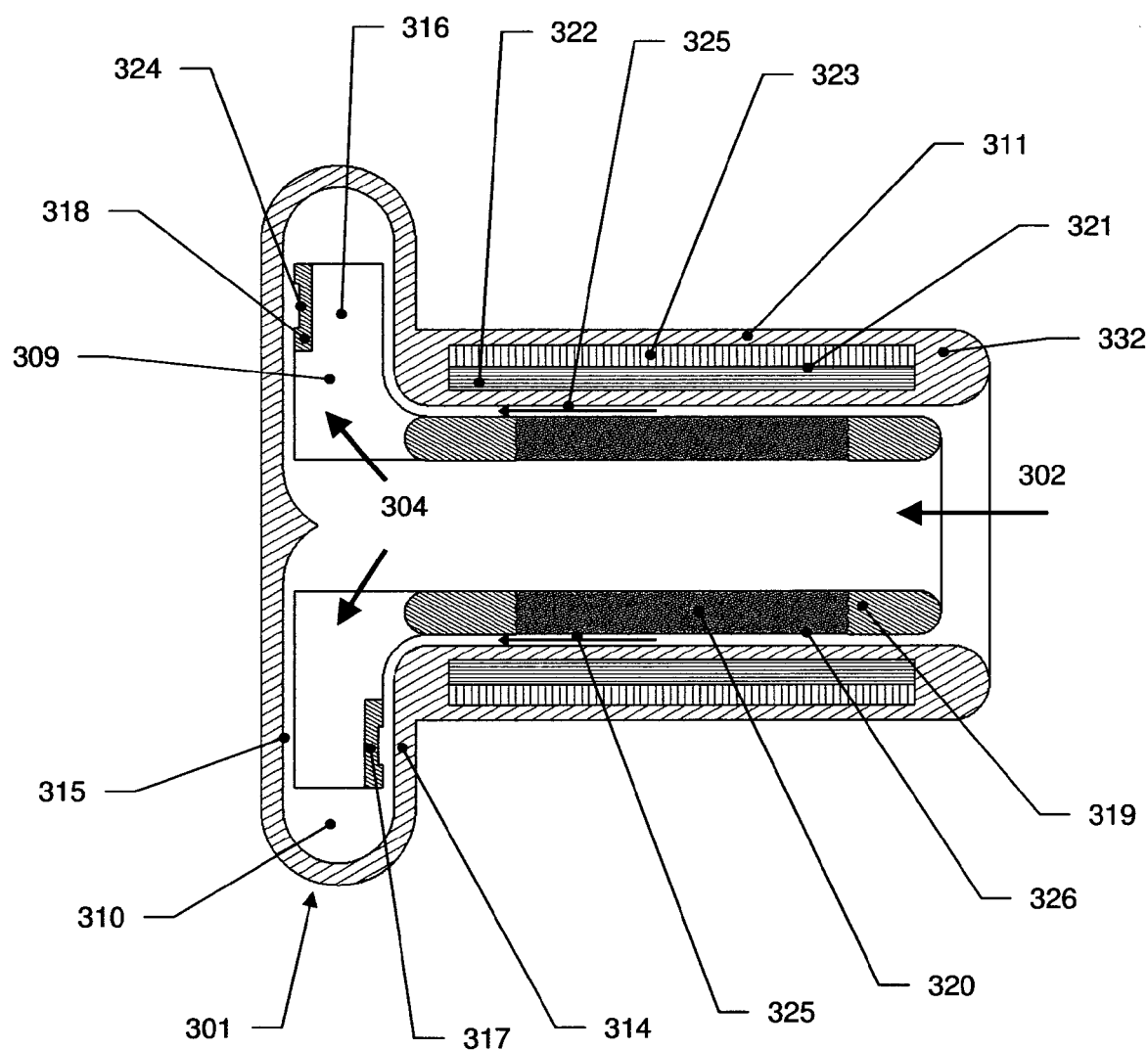
FIG. 9 is a full sectional view of a third embodiment of a VAD according to the invention.

FIG. 9 shows a third embodiment of the invention, which is similar to that of FIGS. 1 to 6 first but differs in the area of the motor rotor. Instead of the discrete rotor magnets 120 of FIGS. 1 to 6, the motor rotor 319 of FIG. 9 is a single piece of magnetisable material that has a magnetised zone 320 in position that co-operates with the motor coils 322.

The use of a single piece of magnetisable material enables a simplified construction and therefore a reduced cost of manufacture. All other aspects of the embodiment of FIG. 9 operate in a similar manner to that of FIGS. 1 to 6.

Figure 10:
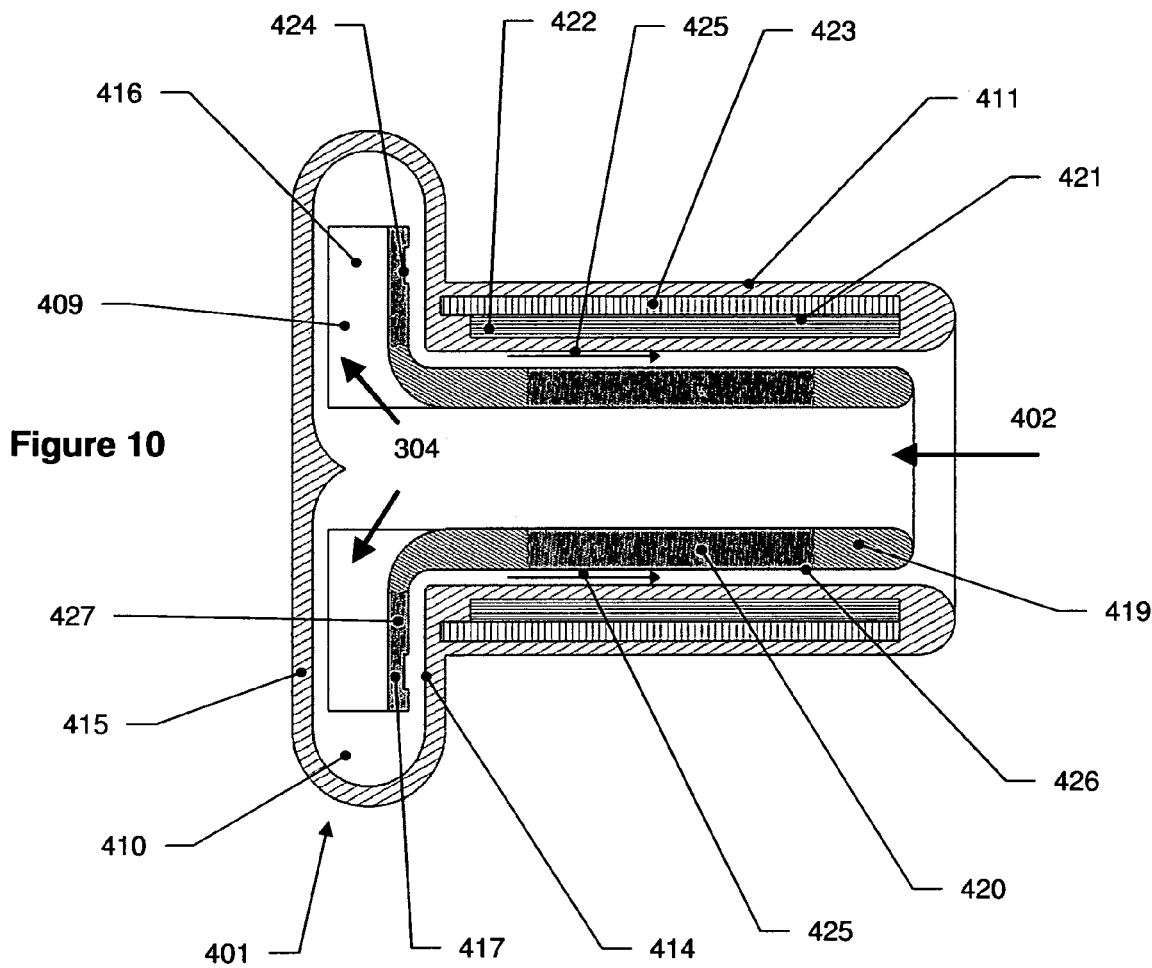
FIG. 10 is a full sectional view of a fourth embodiment of a VAD according to the invention.
Figure 11:
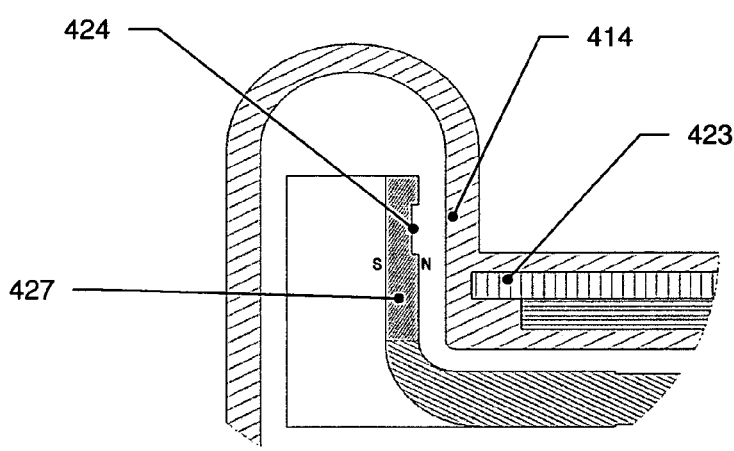
FIG. 11 is a close-up view of a portion of FIG. 10.

FIGS. 10 and 11 show a fourth embodiment, similar to the respective embodiments of FIGS. 7 and 8, and FIG. 9. It has features similar to these embodiments but has differences relative thereto. Specifically, the single front shroud 217 of FIGS. 7 and 8, and the motor rotor 319 all made from a single piece of magnetic material as in FIG. 9 are similar. The embodiment of FIGS. 10 and 11 has a motor rotor 419 of a single piece of magnetisable material with two magnetised zones, namely a motor magnetized zone 420 to co-operate with the motor coils, and shroud magnetized zone 427.

The shroud magnetised zone 427 attracts the impeller 409 (and therefore the entire rotor 419) toward the laminations 423. When the pump is operating, the shroud is prevented from contacting the front face 414 of the casing by the opposing hydrodynamic bearings 424. The magnetic attraction forces and the hydrodynamic bearing forces will reach a stable equilibrium and maintain a clearance between the front shroud 417 and the front face 414 of the casing.

Because the axial position of the rotor 419 is entirely controlled by the combination of the magnetic attraction between the shroud magnetized zone 427 and the laminations 423, and the opposing force from the hydrodynamic bearings 424, no further axial stabilisation is required. Therefore the alternate rear shrouds 118,318 of FIGS. 1 to 6, and FIG. 9, and the flange 231 of FIGS. 7 to 8, are not required.

All other aspects of the embodiment of FIGS. 10 and 11 operate in a similar manner to the previous embodiments.

Figure 12:
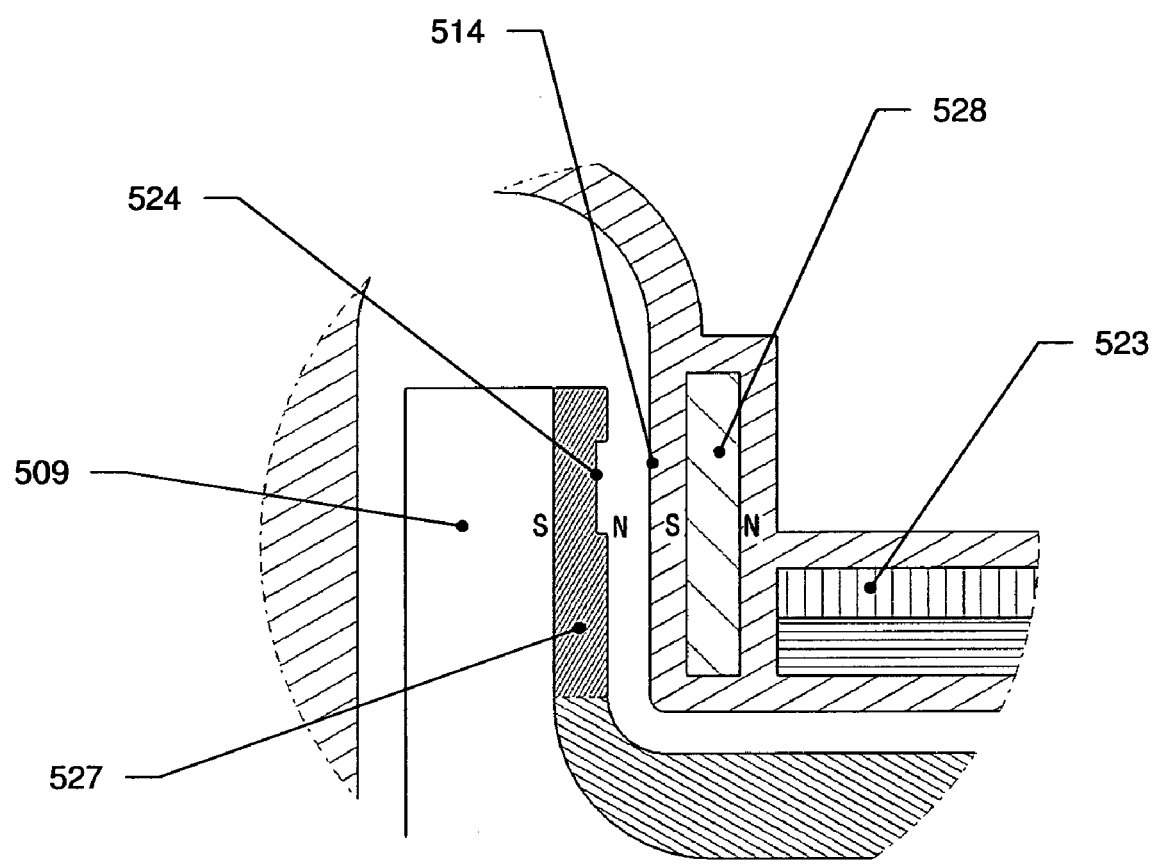
FIG. 12 is a partial sectional view of a fifth embodiment of a VAD according to the invention.

FIG. 12 shows a fifth embodiment which is very similar to that of FIGS. 10 and 11 and differs because of the inclusion of an additional permanent magnet 528 in the casing adjacent to the front face 514. The additional permanent magnet 528 is arranged to provide a stronger attracting force between the magnetized zone 527 on the front shroud 517 of the impeller 509 and therefore provide improved axial positional stability of the impellor 509. The poles of the permanent magnet 528 are opposite to those of the magnetised zone 527 to create an attractive force.

All other aspects of the embodiment of FIG. 12 operate in a similar manner to the embodiment of FIGS. 10 and 11.

Figure 13:
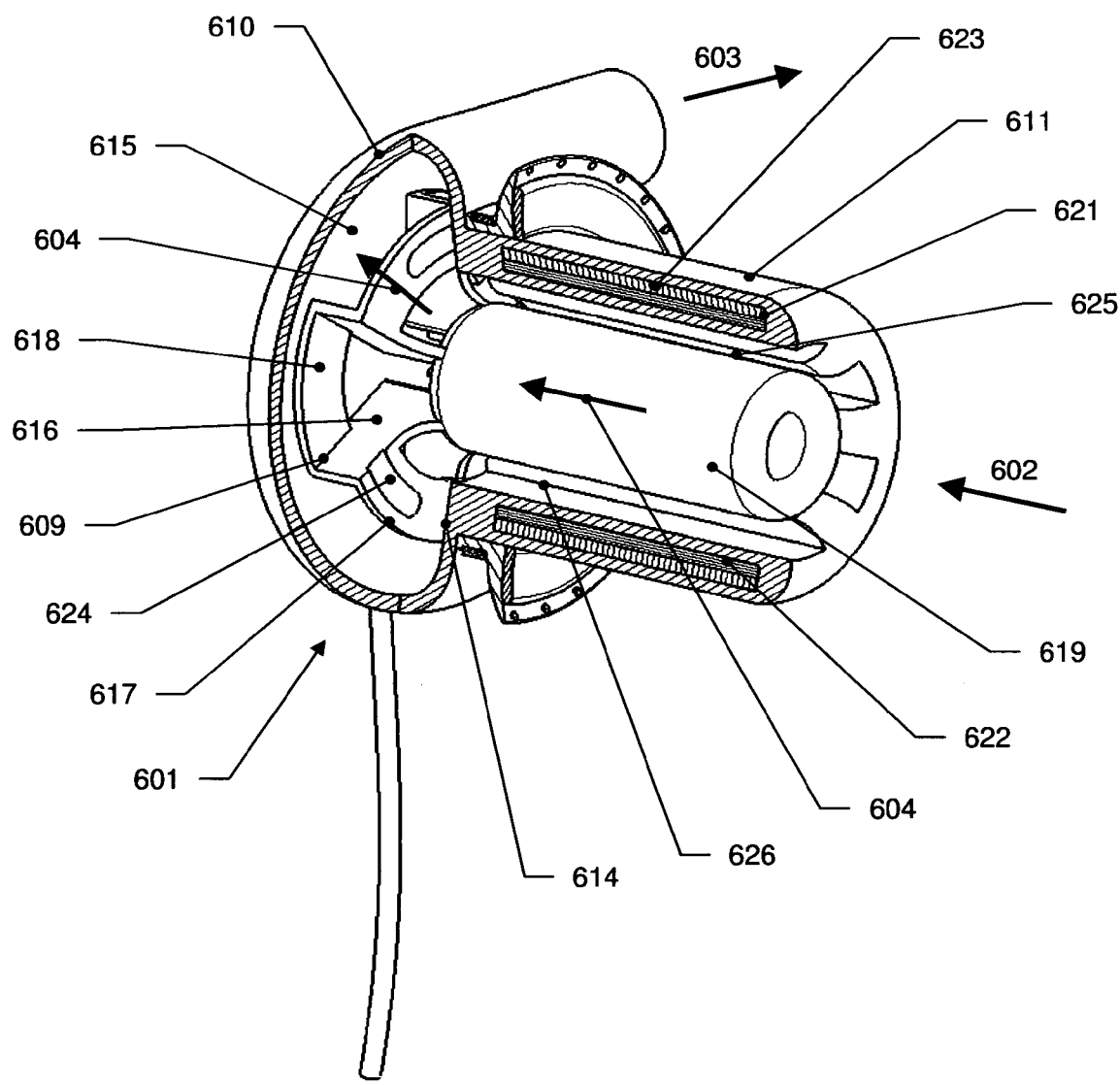
FIG. 13 is a perspective cutaway view of a sixth embodiment of a VAD according to the invention.
Figure 14:
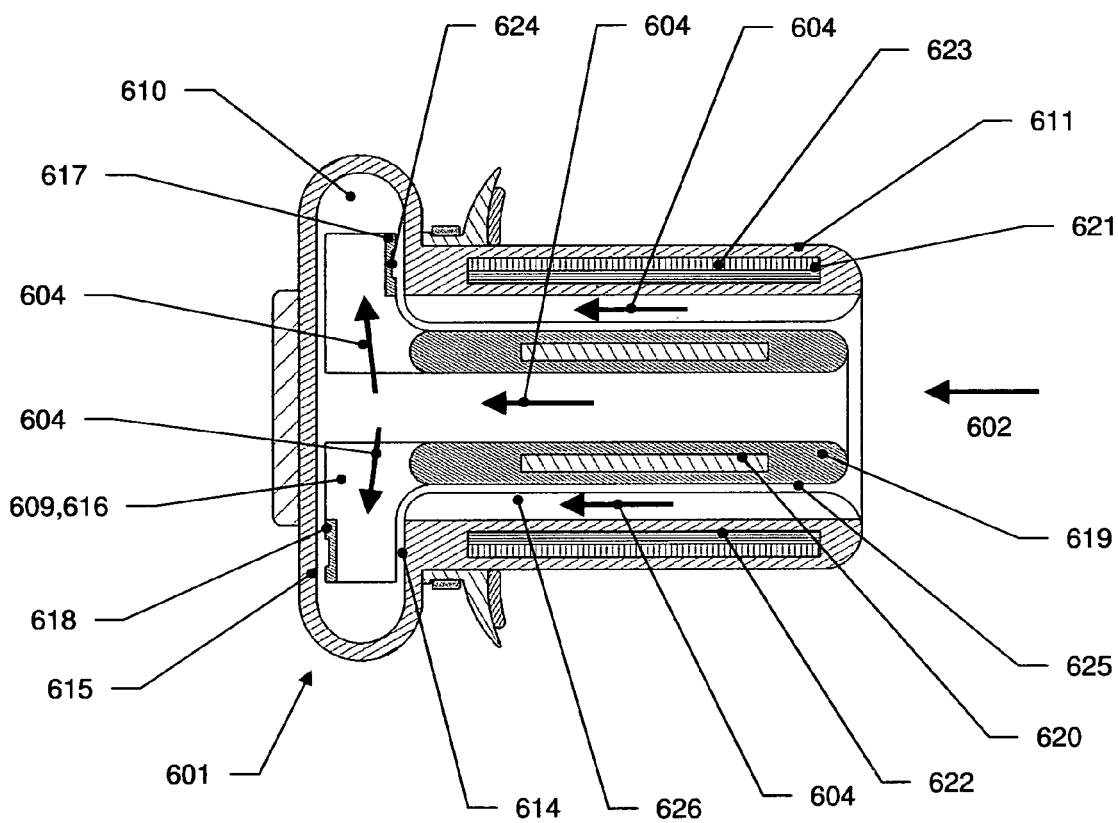
FIG. 14 is a full sectional view of the VAD of FIG. 13.
Figure 15:
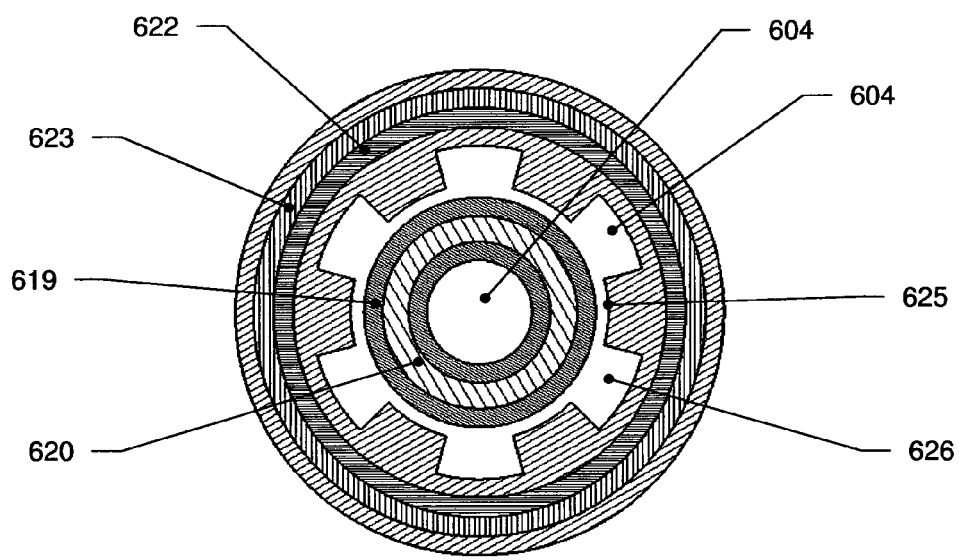
FIG. 15 is a radial sectional view of the VAD of FIG. 13.

FIGS. 13 to 15 show a sixth embodiment of the invention similar to that of FIGS. 1 to 6 but differing in the area of the flow path 604 through the inflow cannula 611. Instead of the discrete primary flow path 104 and secondary flow path 125 of the embodiment of FIGS. 1 to 6, the embodiment of FIGS. 13 to 15 uses a split primary flow path 604 so that more blood can pass through the gap between the motor rotor 619 and motor stator 621. This enables more heat to be removed from the motor so that the temperature rise in the blood removing the heat is minimal.

Simply increasing the radial gap between rotor 619 and stator 621 to promote more flow would impair effectiveness of the bearing 625, because hydrodynamic bearings generally require tight clearances to function properly.

In the embodiment of FIGS. 13 to 15, a series of longitudinally extending grooves 626 is provided in the gap between rotor 619 and stator 621. The grooves 626 allow sufficient volume of blood to flow through them whilst also providing areas of tight clearance between rotor 619 and stator 621 in the land between the grooves 626 suitable for radial hydrodynamic bearings 625.

The hydrodynamic bearings 625 may be created by the clearance in the lands defined between the grooves 626 tapering (decreasing) with respect to the direction of rotation.

All other aspects of the embodiment of FIGS. 13 to 15 operate in a similar manner to the embodiment of FIGS. 1 to 6.

Figure 16:
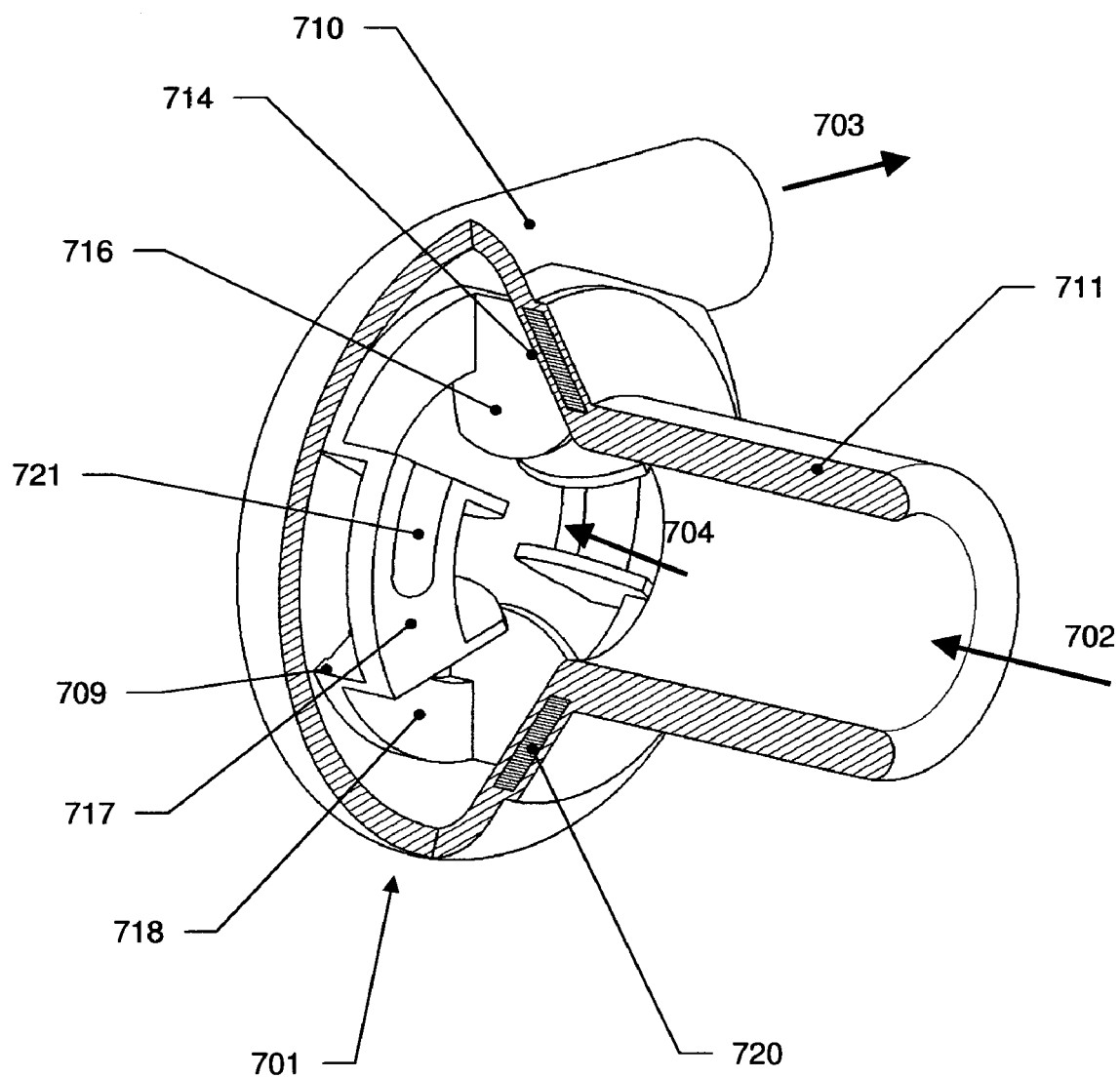
FIG. 16 is a perspective cutaway view of a seventh embodiment of a VAD according to the invention.
Figure 17:
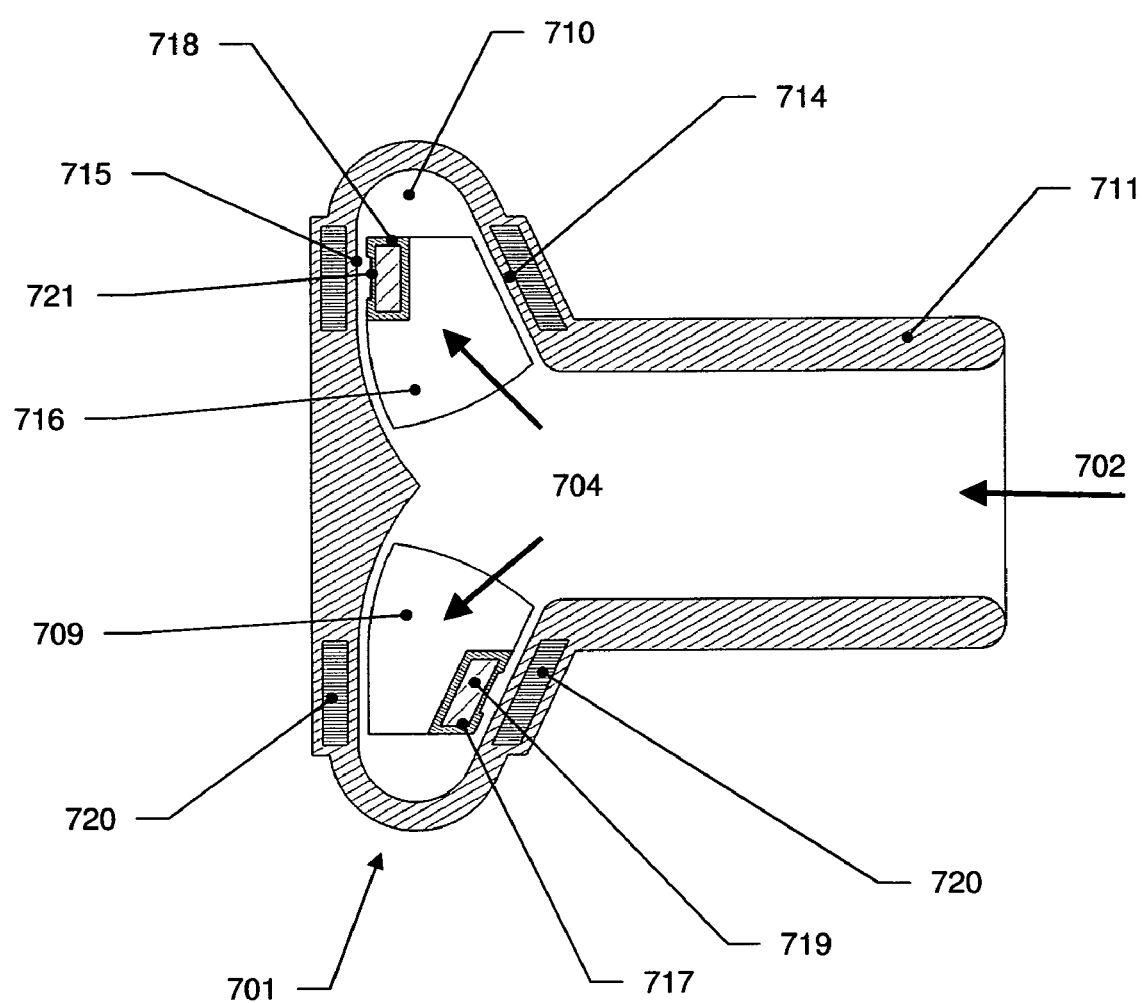
FIG. 17 is a full sectional view of the VAD of FIG. 16.

FIGS. 16 and 17 show a seventh embodiment; this seventh embodiment differs significantly from previous embodiments in some respects. It will therefore be given a more complete description, and reference will be made to previous embodiments where appropriate.

The embodiment of FIGS. 16 and 17 has a pumping chamber 701 with an inlet 702 for blood and an outlet 703 for blood. A primary blood flow path 704 is defined between the inlet 701 and the outlet 702.

Figure 2:
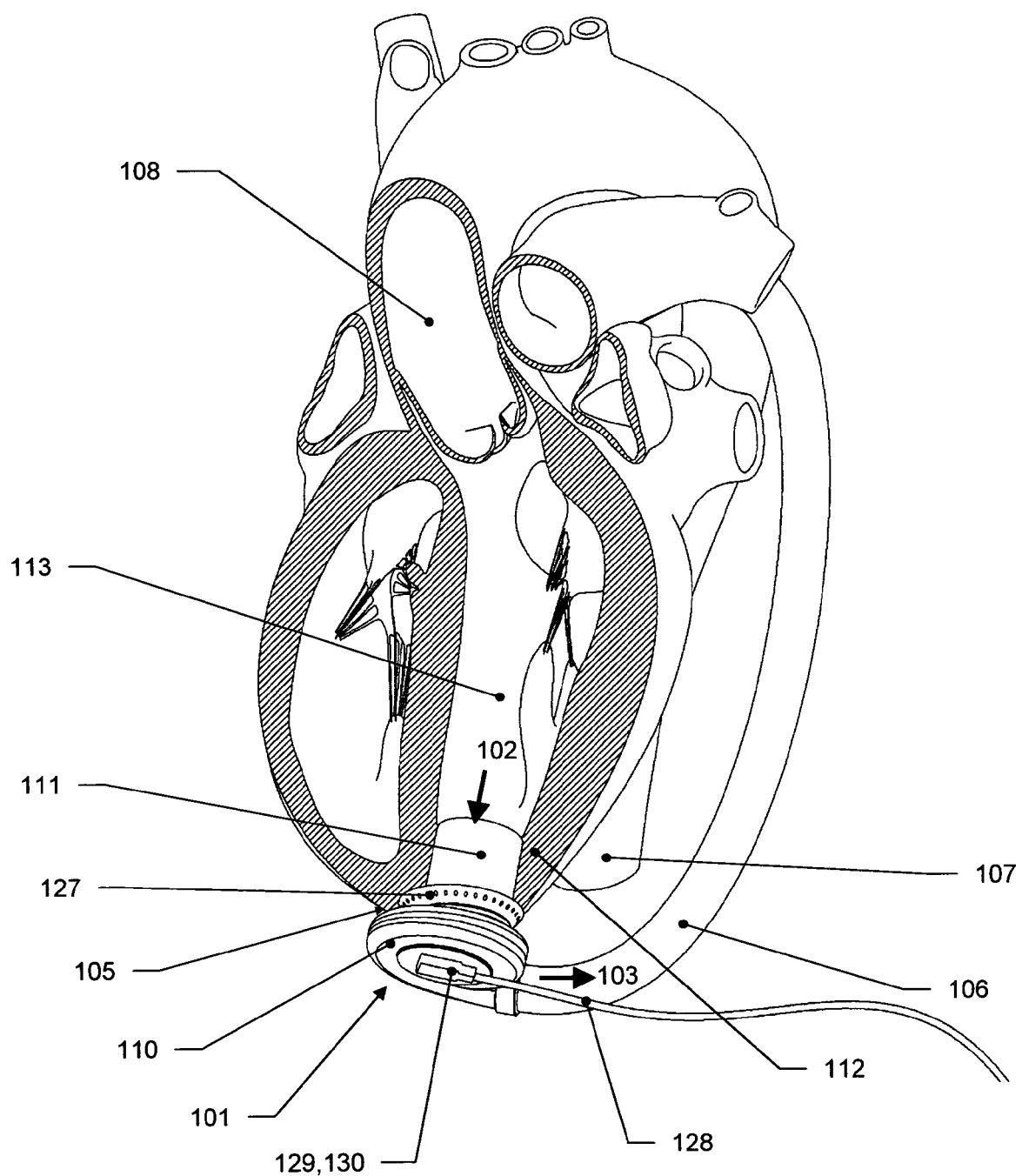
FIG. 2 is a cutaway view of the VAD of FIG. 1 implanted into a human heart.
Figure 3:
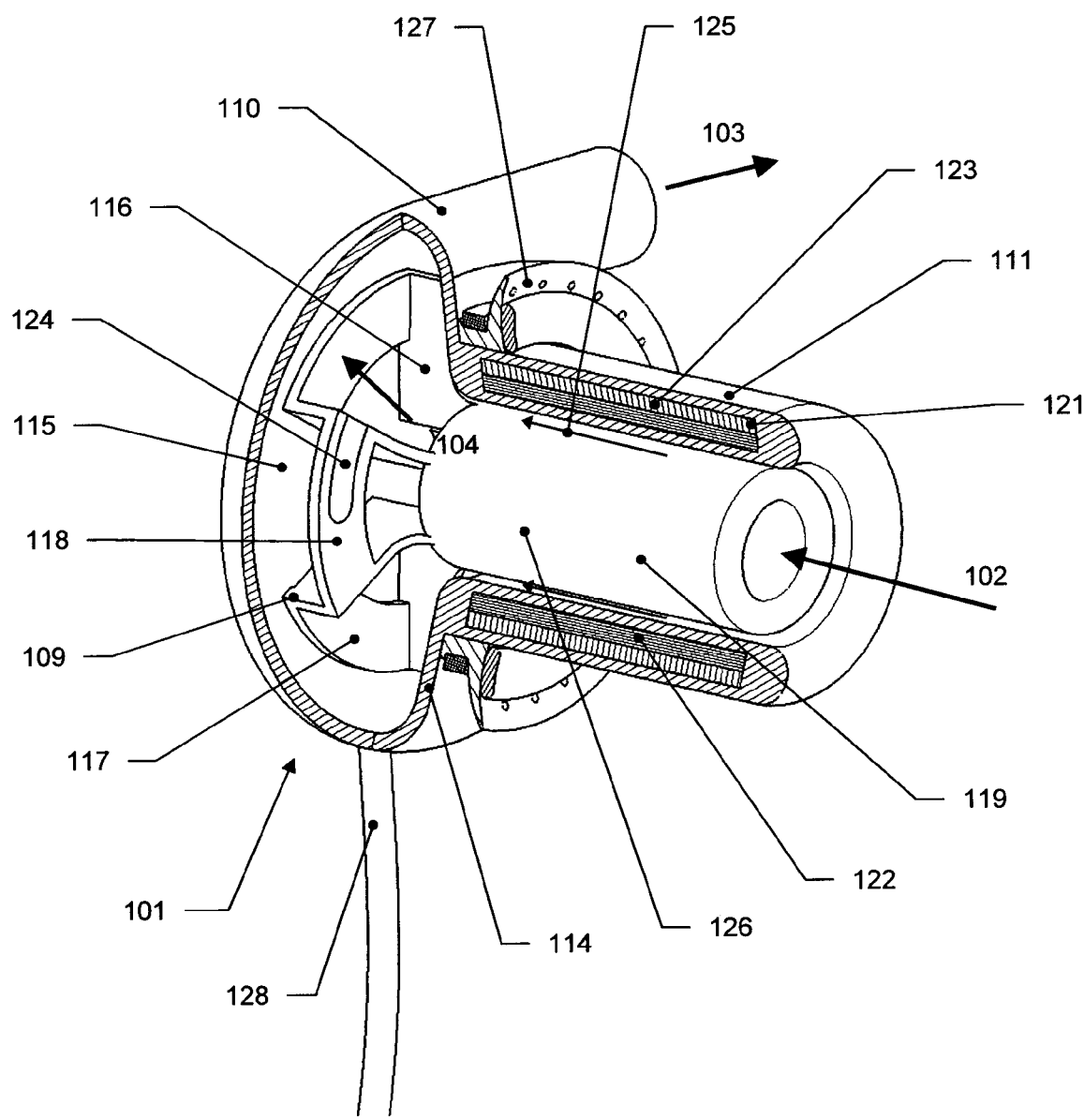
FIG. 3 is a perspective cutaway view of the VAD of FIG. 1.
Figure 4:
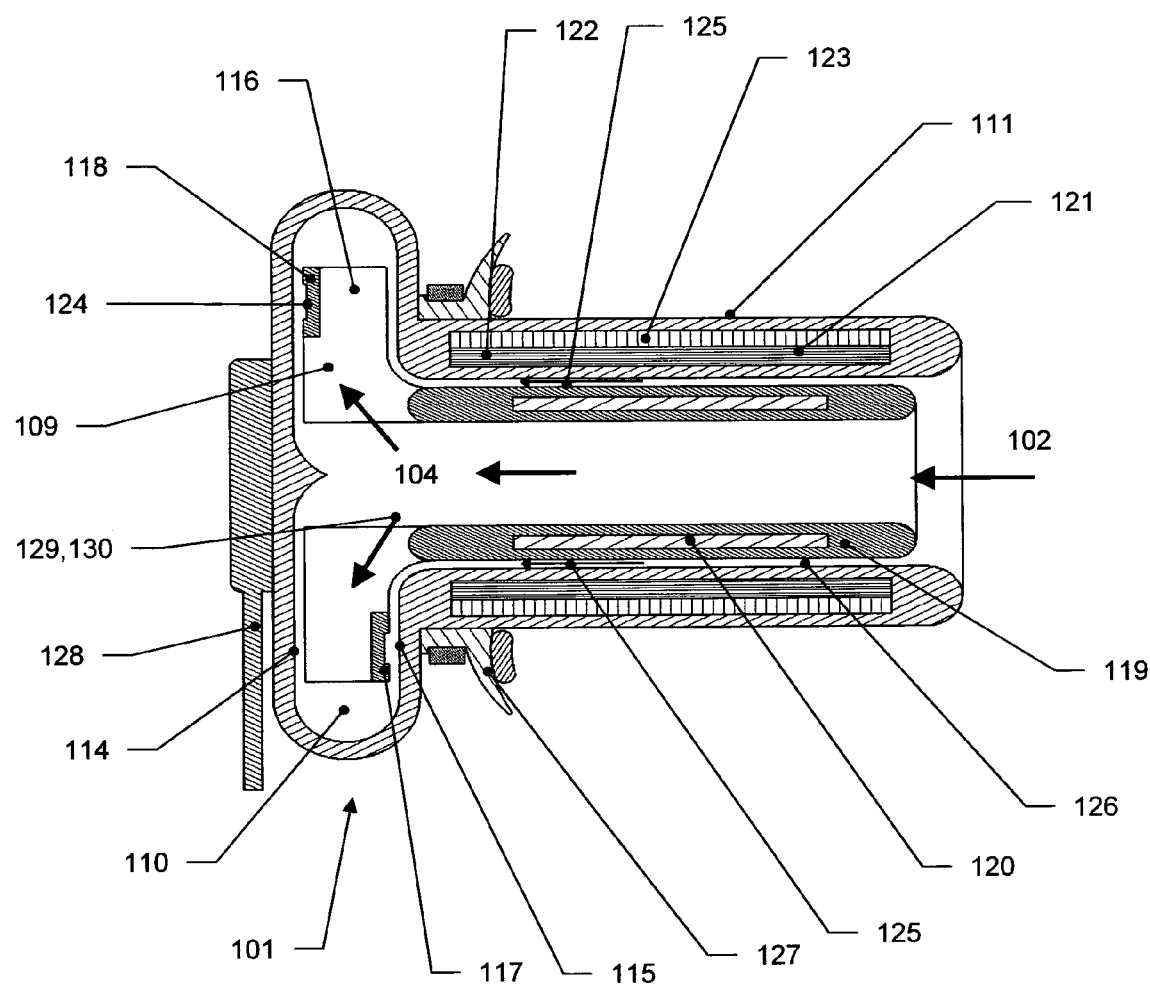
FIG. 4 is a full sectional view of the VAD of FIG. 1.
Figure 5:
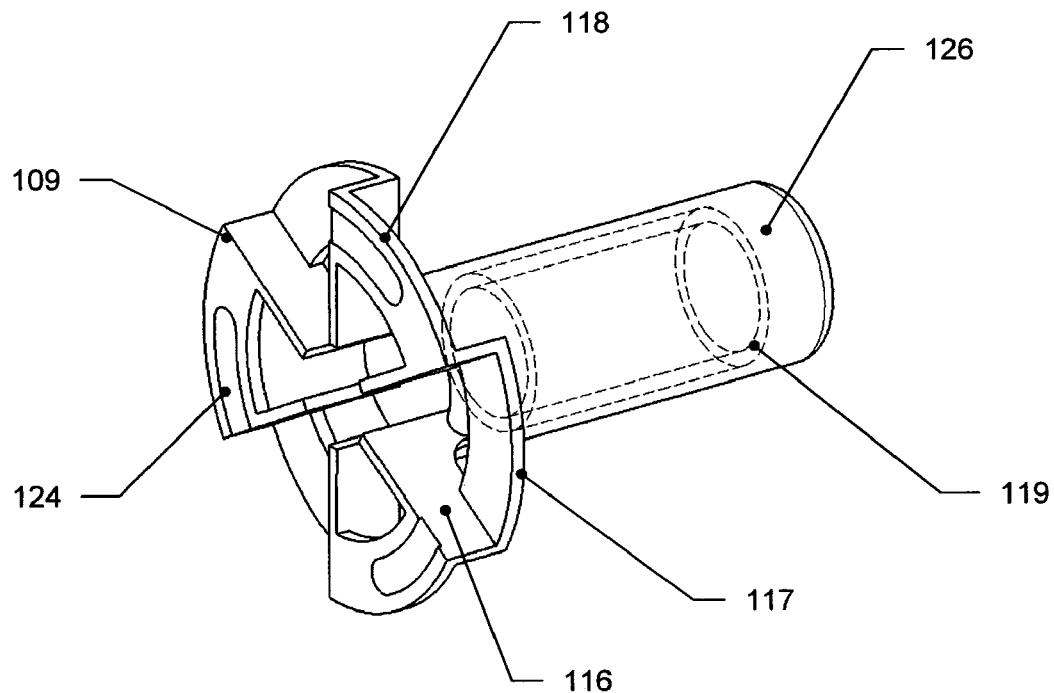
FIG. 5 is a perspective view of only the impeller of the VAD of FIG. 1 from a first viewpoint.
Figure 6:
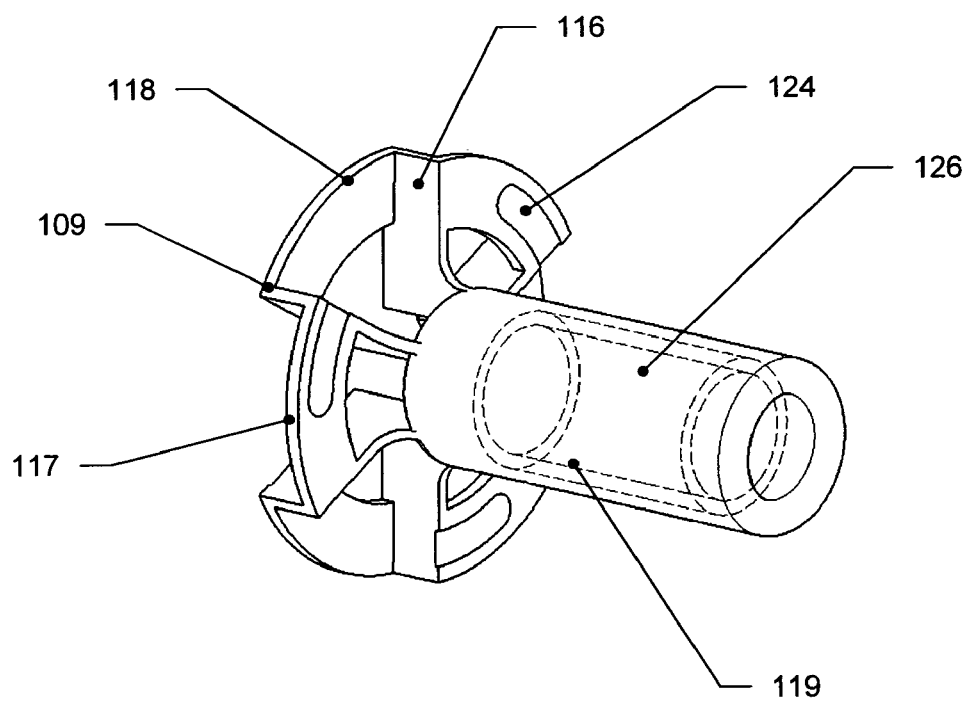
FIG. 6 is perspective view of only the impeller of FIG. 5 from a second viewpoint.

With additional reference to FIG. 2, the pumping chamber 701 resides outside of the heart on the apex of the ventricle 105 with its outlet 703 connected to an outflow cannula 106 which is in turn grafted to the descending aorta 107 (as with previous embodiments). The pumping chamber 701 further includes an impellor 709 which is preferably of a radial or mixed flow type and a volute 710 which aids the conversion of kinetic energy to pressure thus improving efficiency.

An inflow cannula 711 extends from the pumping chamber 701, through the wall of the ventricle 112 into the chamber of the ventricle 113, so that the inlet for blood 704 is completely within the chamber of the ventricle 113. The diameter of the inflow cannula 711 is only as large as is required for the flow of blood and the core required in the ventricle wall 113 to accommodate it is a small as possible.

The pumping chamber 701 is enclosed by a casing or housing that has a front portion 714 adjacent to inflow cannula 711 and a rear portion 715 opposite to inflow cannula 711.

The impeller 709 has a series of impeller blades 716 connected by a shroud that alternately bridges that gap between blades 716 on their front and rear edges. Therefore a series of front shrouds 717 are created on the side of the impeller adjacent to the inflow cannula 711, and a series of rear shrouds 718 are created on the side of the impeller opposite to the inflow cannula 711.

The motor that powers the pump is integrated into the front shrouds 717 and rear shrouds 718 of the impeller 709, and the front portion 714 and rear portion 715 of the casing. The type of motor employed is a permanent magnet brushless DC motor which generally means that the motor rotor contains permanent magnets and the motor stator contains the coils. Therefore the shrouds 717,718 contain the permanent magnets 719, and the casing contains the coils 720. There is no electrical connection between the magnets 719 and the coils 720.

The motor need not necessarily be integrated into both sides 714,715 of the casing and impeller 709, but could instead be integrated into one side only. In this case, in order to provide a sufficiently powerful motor, the impellor shroud (717 or 718) on the chosen portion (714 or 715) can be both thicker and wider than the opposite side to allow larger magnets 719 to be used than would be possible if equally sized and spaced front shrouds 717 and rear shrouds 718 were used.

The faces on the shrouds 717 and rear shrouds 718 are large enough to accommodate hydrodynamic bearings 721 for the centralisation of the impeller in use. The impeller 709 and front shrouds 717 are also inclined so that the hydrodynamic bearings 721 constrain the impeller 709 in both axial and radial directions. This layout restrains all degrees of freedom and means that no further centralisation means is required.

All other aspects of the embodiment of FIGS. 16 and 17 operate in a similar manner to the previously described embodiments. The method of attachment to the heart and the provision of electrical power is as described for the embodiment of FIG. 1.

It is also possible to combine the layout of the embodiment of FIGS. 16 and 17 with the rotor made from a single piece of magnetic material as described in FIG. 9 and FIGS. 10 to 11. This is an eighth embodiment which is illustrated in FIG. 18.

Figure 18:
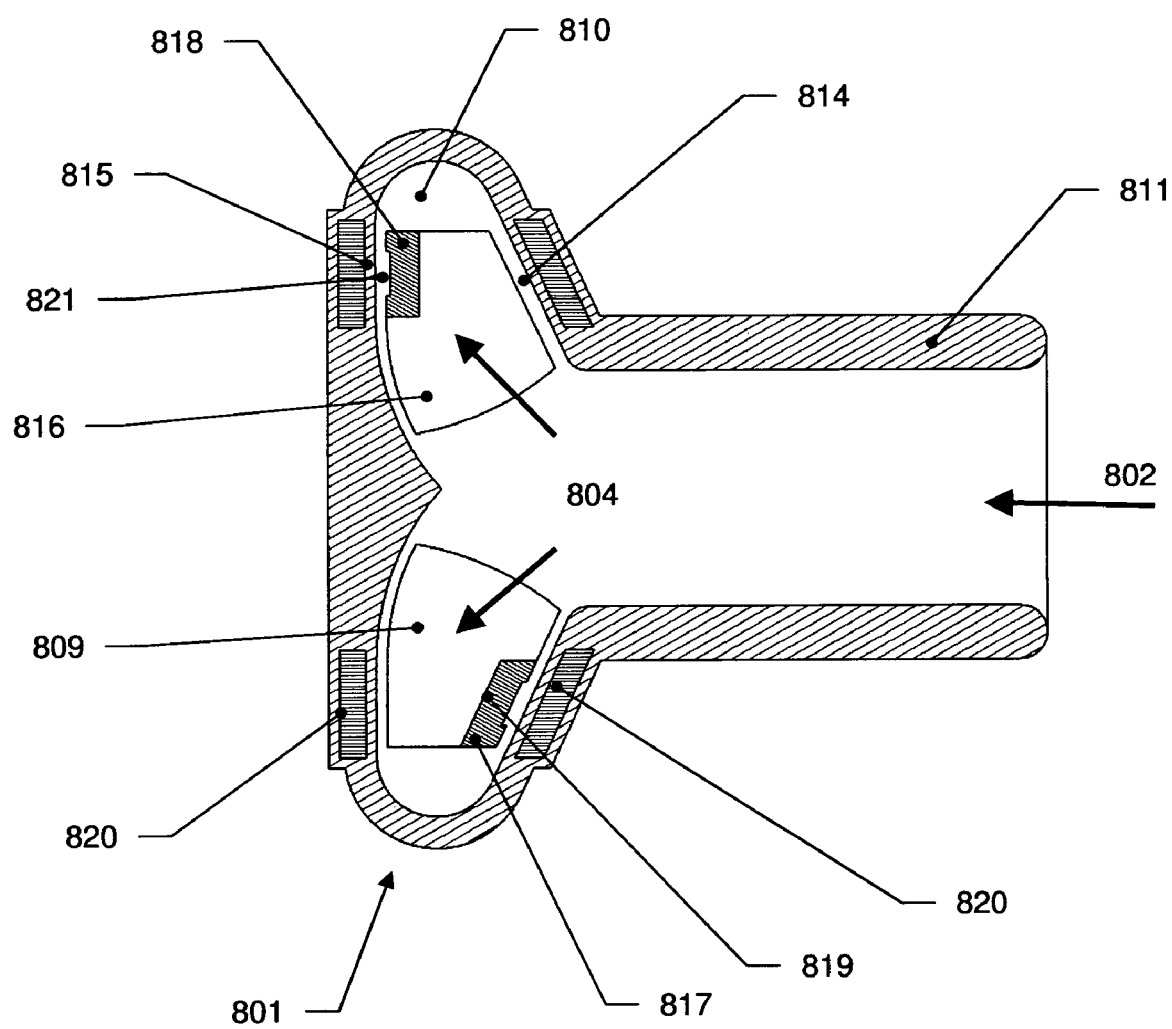
FIG. 18 is a full sectional view of an eighth embodiment of a VAD according to the invention.

The embodiment of FIG. 18 has an impeller 809 of a single piece of magnetisable material and incorporates magnetised zones 819 in the front alternating shrouds 817 and the rear alternating shrouds 818 that correspond with the motor coils 820. The magnetised zones 819 replace the discrete permanent magnets 819 of FIGS. 16 and 17.

Whilst the magnetised zones 819 are shown on both the front alternating shrouds 817 and rear alternating shrouds 818 with two sets of motor coils 820 corresponding to each, it is possible to include magnetised zones 819 in only one of either the front alternating shrouds 817 or the rear alternating shrouds 818. In this case only one set of corresponding coils 820 would be included.

All other aspects of the embodiment of FIG. 18 operate in a similar manner to those of the embodiment of FIGS. 16 and 17.

Figure 19:
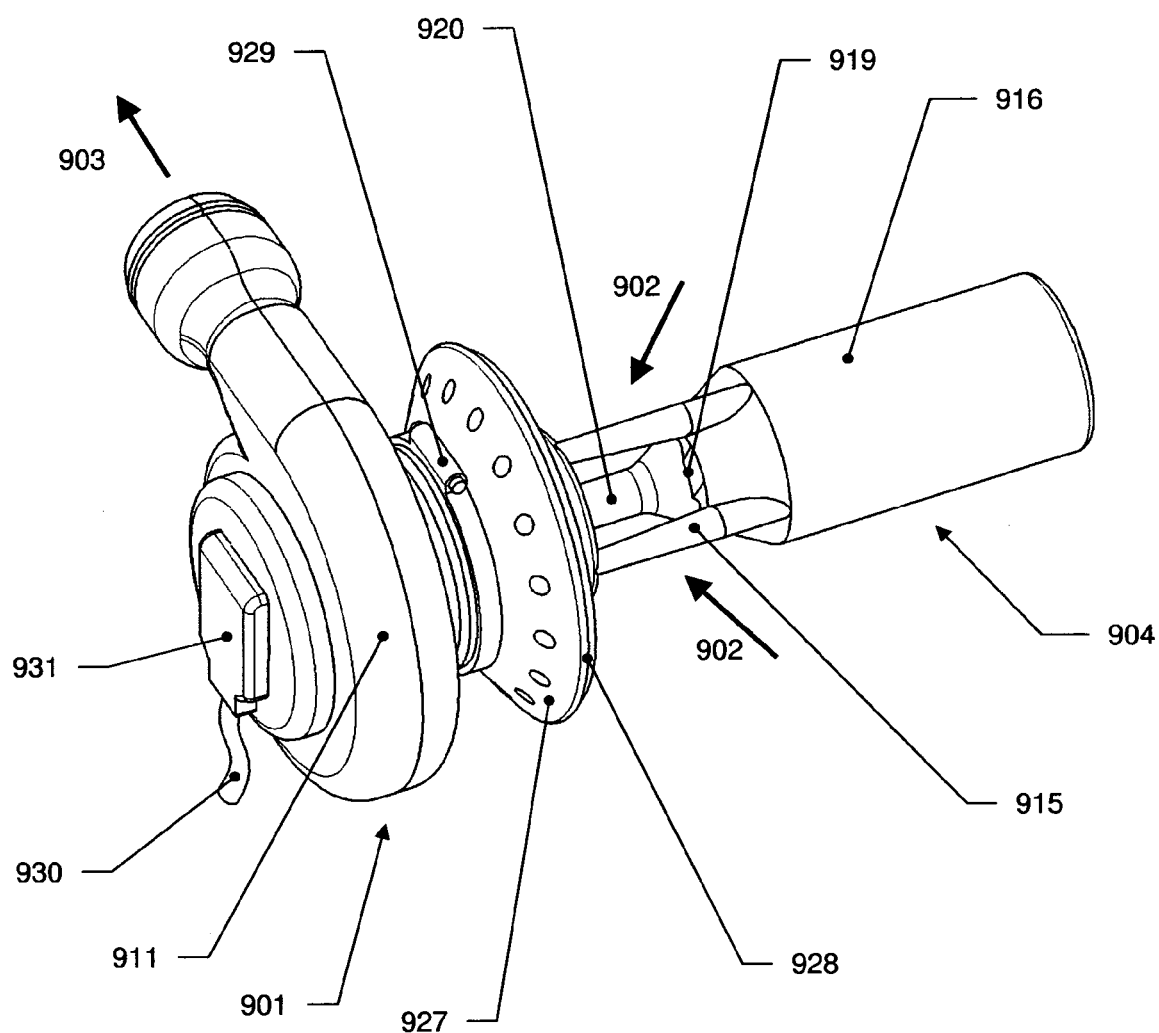
FIG. 19 is a perspective view of a ninth embodiment of a VAD according to the invention.
Figure 20:
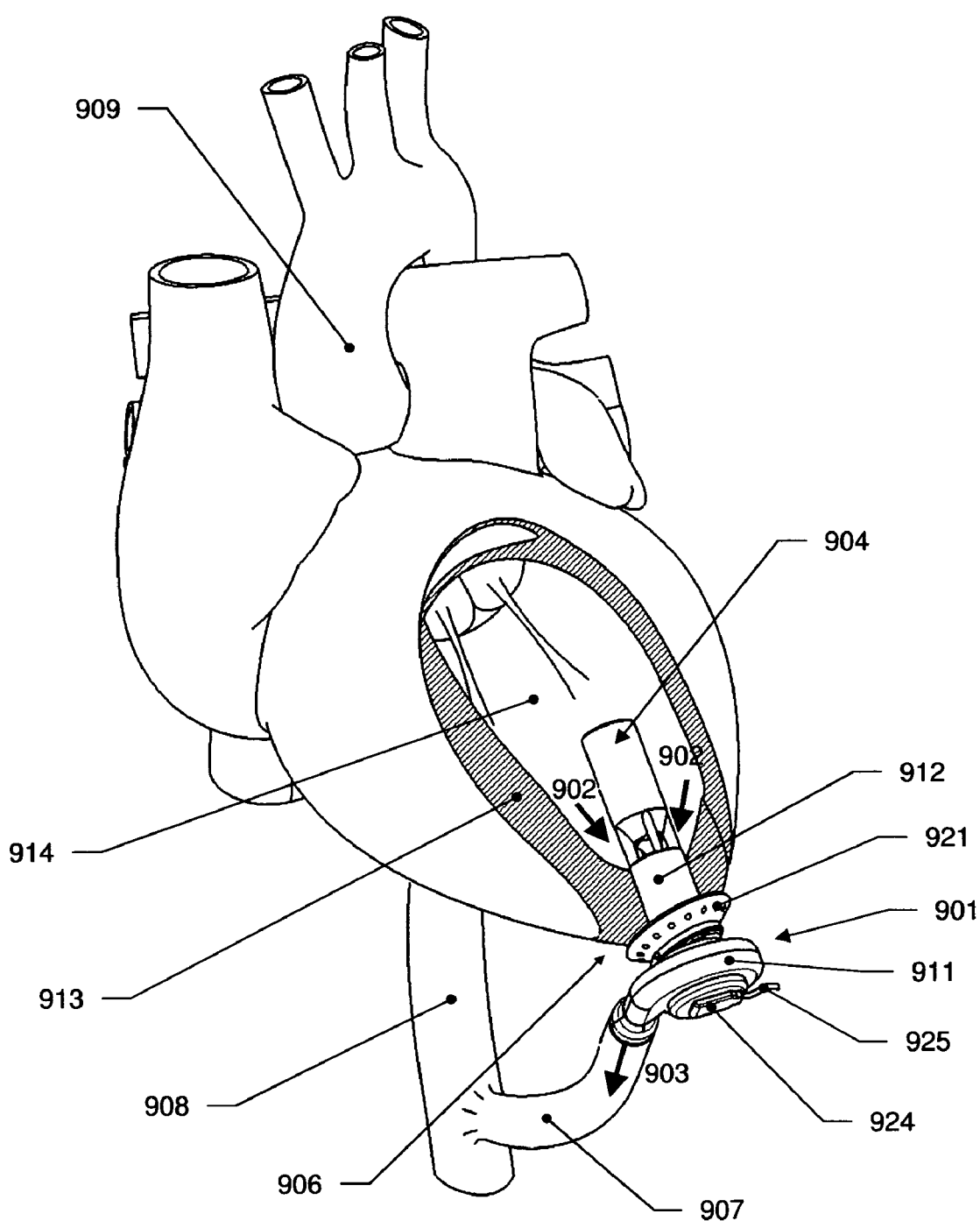
FIG. 20 is a cutaway view of the VAD of FIG. 19 when implanted.
Figure 21:
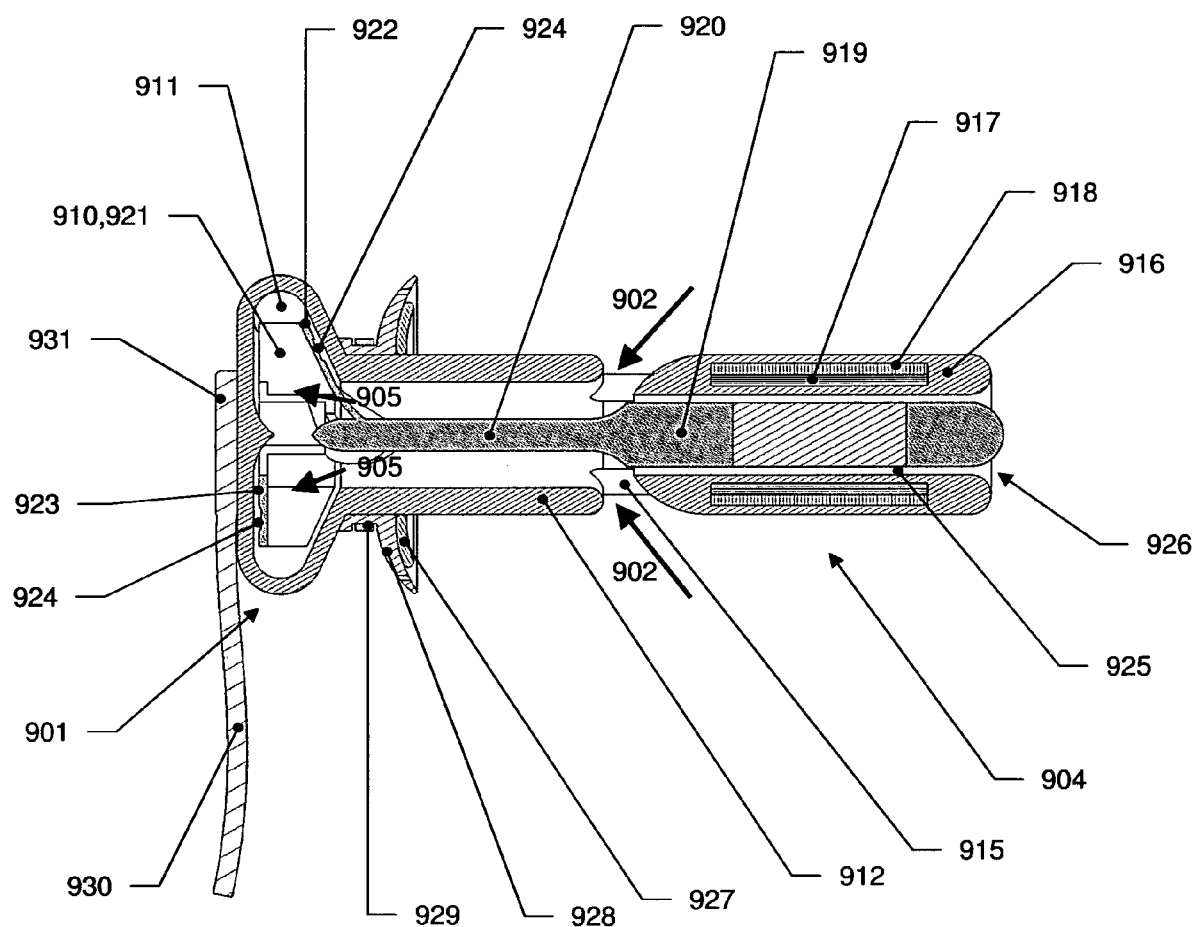
FIG. 21 is a full sectional view of the pump of FIG. 19.

FIGS. 19 to 21 show a ninth embodiment of the invention, which differs significantly from previous embodiments in some respects so it will be given a more complete description, with reference to previous embodiments where appropriate.

The device of FIGS. 19 to 21 has a pumping chamber 901 with an inlet 902 for blood, an outlet 903 for blood, and a motor portion 904. A primary blood flow path 905 is defined between inlet 901 and outlet 902.

The pumping chamber 901 resides outside of the heart on the apex of the ventricle 906 with its outlet 903 connected to an outflow cannula 907 which is in turn grafted to the descending aorta 908. The pumping chamber 901 further has an impeller 910 which is preferably of a radial or mixed flow type and a volute 911. An inflow cannula 912 extends from the pumping chamber 901, through the wall of the ventricle 913 into the chamber of the ventricle 914, so that the inlet for blood 902 is completely within the chamber of the ventricle 914.

The motor portion 904 resides within the chamber of the ventricle 914 and is attached to the inflow cannula by webs 915 that span the inlet 902. The motor portion 904 has a motor stator 916 made up of a motor coil 917 and laminations 918, and a motor rotor magnet 919. The motor layout illustrated is that of a conventional cylindrical brushless DC motor, which is optimal for power and efficiency.

The torque from the motor rotor 919 is transmitted to the impeller by a drive shaft 920 that extends through the centre of the inlet 903. The drive shaft is thin in diameter and does not significantly reduce the cross sectional area available for blood in the inlet 903. Therefore the diameter of the inlet 903 is only as large as is required for the flow of blood and the core required in the ventricle wall 913 to accommodate it is as small as possible.

As with previously described embodiments, the impeller 910 has a series of impeller blades 921 that are connected by a shroud that alternately bridges that gap between the blades 921 on their front and rear edges. Therefore a series of front shrouds 922 is created on the side of the impellor adjacent to the inflow cannula 912, and a series of rear shrouds 923 is on the side of the impeller opposite to the inflow cannula 912.

The faces on the front shrouds 922 and rear shrouds 923 are large enough to accommodate hydrodynamic bearings 924 for the centralisation of the impeller. The impeller 910 and front shrouds 922 are also inclined so that the hydrodynamic bearings 924 constrain the impeller 910 in both axial and radial directions. This layout restrains all degrees of freedom and means that no further centralisation means is required for the impeller 910.

As the motor portion 904 is axially spaced from the impellor 910, the motor rotor 919 will require a means for centralisation in at least the radial aspect. This is achieved by providing a radial hydrodynamic bearing 925 in the clearance between the motor rotor 919 and the motor stator 916. Blood is allowed to flow into through the bearing by the motor portion 904 having an open end 926. The radial hydrodynamic bearing 925 may include additional features to further promote flow therethrough.

The VAD can be attached to the heart by a sewing ring 921, sealing felt 922 clamping means 923 similar to the arrangement described in the embodiment of FIGS. 1 to 6. Electrical power is provided via an electrical cable 924 and connector 925, also similar to the arrangement described in the embodiment of FIGS. 1 to 6. A surgical procedure to fit any embodiment of the VAD according to the invention would typically comprise the following steps:

A mini thoracotomy is used to gain access to the apex 105 of the left ventricle;

Traction is then placed on the heart to stabilise it positionally;

The sewing ring 127 is then attached to the apex 105 (note that this is carried out whilst the heart is still functioning—bypass is not required);

A core is then made in the wall of the ventricle;

The device is then introduced into the heart through the core;

A clamping is then tightened setting the position of the device;

The outflow cannula 106 is then grafted to the aorta (the outflow graft may be carried out earlier in the procedure and then connected to the outlet of the VAD later); and The power cable 128 is then routed to a suitable exit point (or to an implantable inductive coil); and then the initial thoracotomy is closed.

The invention claimed is:

1. Heart assist apparatus suitable for implantation into a ventricle of a human heart, the apparatus comprising:
   (a) a pump comprising a housing having therein a radial impeller having a series of impeller blades arranged such there is a plurality of odd numbered impeller blades and a plurality of even numbered impeller blades alternating with said odd numbered impeller blades, and a rotor for driving said impeller, both said rotor and said impeller being arranged to be hydrodynamically suspended within the housing, the pump further including a stator for driving said rotor;
   (b) an inlet cannula section arranged to extend from an internal part of the ventricle to straddle the wall of the ventricle, the stator being within said inlet cannula section so as to be located in said internal part of the ventricle when said apparatus is implanted in said ventricle;
   (c) an outlet for blood driven by said impeller, said outlet being substantially transverse to said inlet cannula section, both said outlet and said impeller being arranged to reside outside of the heart when said apparatus is implanted in said ventricle, and
   (d) a shroud comprising a series of alternating front shroud members for alternate even-numbered ones of the impeller blades and a series of alternating rear shroud members for alternate odd-numbered ones of the impeller blades, each said blade being connected to an adjacent blade by a respective alternating one of the shroud members.

2. Apparatus according to claim 1, which further comprises a fixture for fixing the apparatus to a wall of the heart.

3. Apparatus according to claim 1, which has a first blood path from said inlet to said outlet via said impeller, and a second blood path from said inlet to said outlet, said second blood path comprising spacing between said rotor and said stator.

4. Apparatus according to claim 3, wherein the stator has a series of longitudinally extending grooves on an inner face thereof which series of grooves defines the second blood path.

5. Apparatus according to claim 4, which includes respective lands between adjacent ones of the grooves, said lands being provided with hydrodynamic bearings for the stator.

6. Apparatus according to claim 5, wherein said grooves are parallel to one another and extend parallel to a central axis of the stator.

7. Apparatus according to claim 1, wherein motor rotor magnets are incorporated into the alternating shroud members.

8. Apparatus according to claim 1, wherein hydrodynamic bearings are provided on faces of the shroud members adjacent to the pump housing.

9. Apparatus according to claim 8, wherein the hydrodynamic bearings are tapered so as to decrease the clearance between the shroud members and the housing with respect the direction of rotation.

10. Apparatus according to claim 1, which includes a magnetic bias for biasing said impeller towards the stator.

11. Apparatus according to claim 1, wherein said impeller comprises a unitary body of magnetizable material, having magnetized zones for operation of said rotor.

12. Apparatus according to claim 1, which is arranged such that the pump housing is to be located outside of the heart, an inlet cannula is to be located across the wall of the heart, and the rotor is to be located within the heart.

13. Heart assist apparatus suitable for implantation into a ventricle of a human heart, the apparatus comprising:
    (a) a pump comprising a housing having therein a radial impeller having a series of impeller blades arranged such there is a plurality of odd numbered impeller blades and a plurality of even numbered impeller blades alternating with said odd numbered impeller blades, and a motor for driving said impeller, said impeller being arranged to be hydrodynamically suspended within the housing;
    (b) an inlet cannula section arranged to extend from an internal part of the ventricle to straddle the wall of the ventricle, said inlet cannula section having an inlet located in said internal part of the ventricle when said apparatus is implanted in said ventricle;
    (c) an outlet for blood driven by said impeller, said outlet being substantially transverse to said inlet cannula section, both said outlet and said impeller being arranged to reside outside of the heart when said apparatus is implanted in said ventricle, and
    (d) a shroud comprising a series of alternating front shroud members for alternate even-numbered ones of the impeller blades and a series of alternating rear shroud members for alternate odd-numbered ones of the impeller blades, each said blade being connected to an adjacent blade by a respective alternating one of the shroud members.

14. Apparatus according to claim 13, which further comprises a fixture for fixing the apparatus to a wall of the heart.

15. Apparatus according to claim 13, wherein the motor comprises a rotor and a stator for driving said rotor, in which the apparatus has a first blood path from said inlet to said outlet via said impeller, and a second blood path from said inlet to said outlet, said second blood path comprising spacing between said rotor and said stator.

16. Apparatus according to claim 15, wherein the stator has a series of longitudinally extending grooves on an inner face thereof which series of grooves defines the second blood path.

17. Apparatus according to claim 16, which includes respective lands between adjacent ones of the grooves, said lands being provided with hydrodynamic bearings for the stator.

18. Apparatus according to claim 17, wherein said grooves are parallel to one another and extend parallel to a central axis of the stator.

19. Apparatus according to claim 13, wherein said motor includes rotor magnets incorporated into the alternating shroud members.

20. Apparatus according to claim 13, wherein hydrodynamic bearings are provided on faces of the shroud members adjacent to the pump housing.

21. Apparatus according to claim 20, wherein the hydrodynamic bearings are tapered so as to decrease the clearance between the shroud members and the housing with respect the direction of rotation.

22. Apparatus according to claim 13, which includes a magnetic bias for biasing said impeller towards the stator.

23. Apparatus according to claim 13, wherein said impeller comprises a unitary body of magnetizable material, having magnetized zones for operation of said motor.

24. Apparatus according to claim 13, which is arranged such that the pump housing is to be located outside of the heart, an inlet cannula is to be located across the wall of the heart, and the motor is to be located within the heart.

* * * * *